(12) United States Patent
Feldman et al.

(10) Patent No.: US 6,408,848 B1
(45) Date of Patent: Jun. 25, 2002

(54) METHOD AND APPARATUS FOR CONVENIENTLY SETTING A PREDETERMINED VOLUME FOR RE-BREATHING

(75) Inventors: Barry J. Feldman, Plano, TX (US); Anthony T. Pierry, Plantsville, CT (US); William J. Wohltmann, San Jose, CA (US); John A. Triunfo, Jr., Fairfield, CT (US)

(73) Assignee: NTC Technology, Inc., Wilmington, DE (US)

( * ) Notice: Subject to any disclaimer, the term of this patent is extended or adjusted under 35 U.S.C. 154(b) by 0 days.

(21) Appl. No.: 09/537,028

(22) Filed: Mar. 28, 2000

(51) Int. Cl.$^7$ ................................................. A62B 9/00
(52) U.S. Cl. .......................... 128/205.14; 128/200.22; 128/200.24; 128/205.16; 138/121; 138/173; 138/DIG. 8
(58) Field of Search ........................... 128/911, 205.14, 128/205.13, 205.15, 205.16, 200.24, 200.22; 138/121, 173, DIG. 8

(56) References Cited

U.S. PATENT DOCUMENTS

| | | | | |
|---|---|---|---|---|
| 4,269,196 A | * | 5/1981 | Toms et al. | 128/205.23 |
| 5,623,922 A | * | 4/1997 | Smith | 128/204.17 |
| 5,823,184 A | * | 10/1998 | Gross | 128/204.18 |
| 5,983,896 A | * | 11/1999 | Fukunaga et al. | 128/202.27 |

OTHER PUBLICATIONS

Patent Application and Drawing for U.S. Patent Application Ser. No. 09/173,517 filed Oct. 15, 1998, pending.
Patent Application and Drawing for U.S. Patent Application Ser. No. 08/770,138 filed Dec. 19, 1996, pending.
Patent Application and Drawing for U.S. Patent Application Ser. No. 09/262,510 filed Mar. 2, 1999, pending.

* cited by examiner

Primary Examiner—John G. Weiss
Assistant Examiner—Darwin P. Erezo
(74) Attorney, Agent, or Firm—TraskBritt

(57) ABSTRACT

The present invention provides a method and device for conveniently setting the volume of a variable-length tubing loop used in a re-breathing circuit to various selected predetermined values. The device includes a card of an inelastic, disposable material which is attachable to a portion of the tubing loop or adjacent structure and which has marked on it several positions to which the tubing loop can be extended to set the volume of the loop at selected predetermined values. The card is preferably formed of a substantially rigid material which may be configured to fold around the tubing loop and adjacent structures to provide support and protection during shipping and handling of the device. The card may include instructions for use of the tubing loop printed on an outer surface thereof. Some or all of the card may be detachable from the tubing loop so that once the desired tubing volume is set, all or a portion of the card may be removed and disposed of.

23 Claims, 5 Drawing Sheets

US 6,408,848 B1

METHOD AND APPARATUS FOR CONVENIENTLY SETTING A PREDETERMINED VOLUME FOR RE-BREATHING

BACKGROUND OF THE INVENTION

1. Field of the Invention

This invention relates to non-invasive approaches for determining cardiac output in patients, specifically to re-breathing techniques for determining cardiac output in patients, and most particularly to methods and devices for setting the volume of gases to be re-breathed by a patient.

2. Statement of the Art

It is frequently desirable to monitor a patient's cardiac output during medical and surgical procedures. Non-invasive cardiac output (NICO) techniques are rapidly gaining favor. Re-breathing methods are particularly advantageous because they are non-invasive, use the accepted Fick principle of calculation, are easily automated, allow cardiac output to be calculated from commonly monitored clinical signals, and, if a partial re-breathing technique is used, require no patient cooperation.

In re-breathing methods, a modified form of the Fick Equation may be used to estimate cardiac output from observed changes in expired $CO_2$ ("$pCO_2$"), which corresponds to arterial $CO_2$. A comparison is made between a "standard" ventilation event and a sudden change in ventilation which causes a change in expired $CO_2$ values and a change in excreted volume of $CO_2$. The sudden change in ventilation is accomplished by causing the ventilated patient to re-breath a specified amount of previously exhaled air.

Conventional re-breathing circuits provide only a fixed re-breathing volume, which may not be optimum, or even suitable, for patients of various sizes and respiratory capacities and resistances to minimize or eliminate interference with the ventilator function. It is also known to employ a variable volume for re-breathing, as disclosed and claimed in U.S. patent application Ser. No. 08/770,138, filed Dec. 19, 1996, assigned to the assignee of the present invention and the disclosure of which application is hereby incorporated herein by this reference. One preferred approach to providing a variable volume for re-breathing as disclosed in the aforementioned application is to employ a variable-length (and thus volume) loop of tubing connected at both ends to a ventilator or breathing circuit by means of a so-called airway valve. Particularly suitable airway valve configurations are disclosed and claimed in U.S. patent application Ser. No. 09/173,517, filed Oct. 15, 1998, assigned to the assignee of the present invention and the disclosure of which is incorporated herein by this reference. It would be advantageous to have a convenient method for setting the volume of such a tubing loop to various predetermined values corresponding to different patient respiratory parameters. Pre-setting the tubing loop volume is advantageous because it minimizes the adjustments required after the tubing loop is in use. In some cases it would also be desirable to provide protection and support for the variable-length tubing loop and associated structures, such as the airway valve and various actuation and monitoring tubing employed during re-breathing, during shipping and handling. It is further desirable to provide instructions for correct use and adjustment of the variable length tubing loop displayed prominently and connected directly to the tubing loop, to minimize the potential for incorrect use of the device. It may also be advantageous to provide instructions for use of monitoring or other equipment used with the inventive device. Finally, it would be desirable for the device used to set the volume of the tubing loop to add little or no additional equipment to the re-breathing system. These and other advantages are provided by the present invention.

SUMMARY OF THE INVENTION

The present invention provides a method and device for conveniently and economically setting the volume of a variable-length tubing loop used in a re-breathing circuit to various predetermined values. The device includes a card of non-elastic, disposable material which is attached to the a portion of the tubing loop or to an adjacent structure and which has marked on it indicia corresponding to several positions to which the tubing loop can be extended in length to set the volume of the loop at different, selected, predetermined values. The card may be configured to fold around the tubing loop and adjacent structures to provide support and protection during shipping and handling of the assembly. The card preferably has instructions for correct use and adjustment of the tubing loop printed on it. Instructions for use of a monitoring device, or other instructions may be printed on the card as well. Some or all of the card may be removable from the tubing loop so that once the desired tubing volume is set, a portion or all of the card may be detached and disposed of.

DETAILED DESCRIPTION OF THE INVENTION

Figure 1:
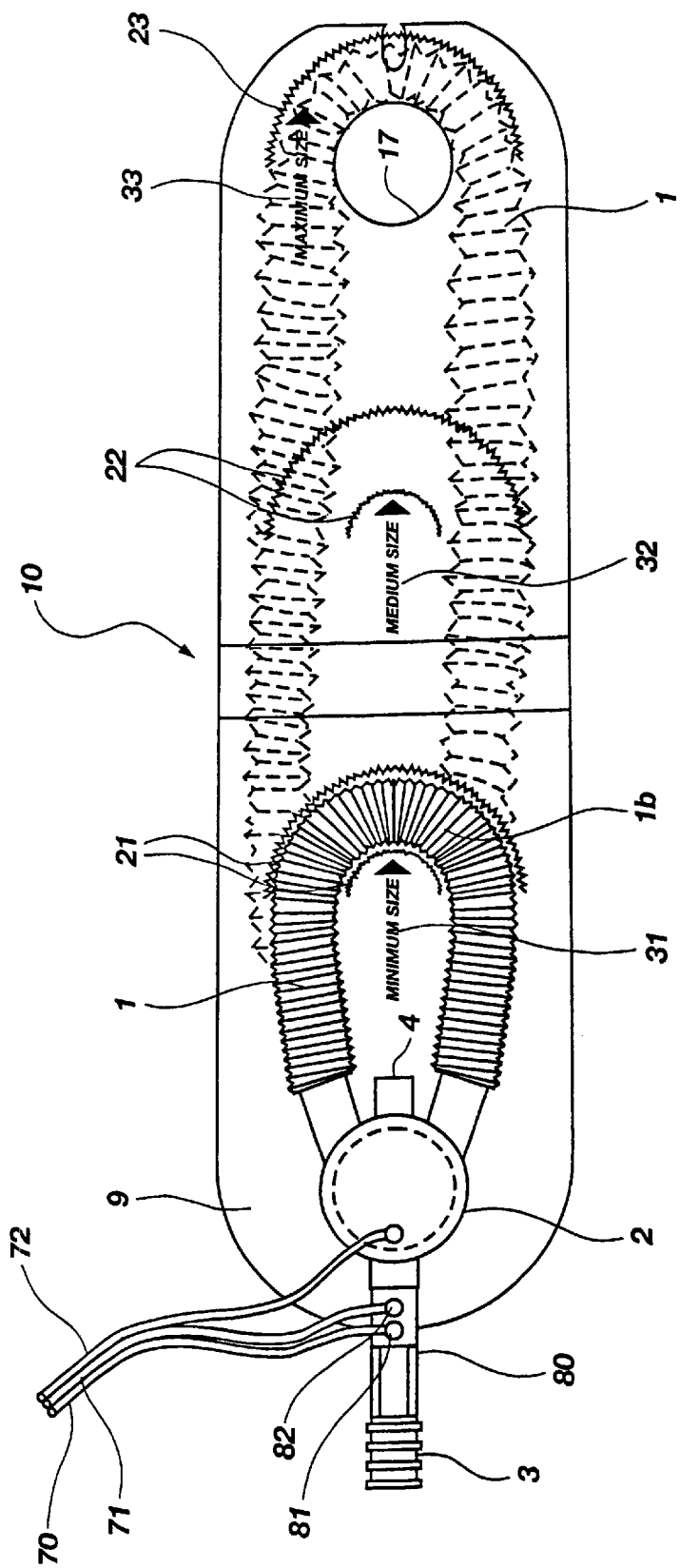
FIG. 1 shows the inventive device in use for adjusting the length of a variable-length tubing loop of a tubing loop and airway valve assembly.

A first embodiment of the invention is depicted in FIG. 1. A variable volume for containing expired gases for use in re-breathing is provided by variable-length, corrugated tubing loop 1. The two ends of tubing loop 1 attach to airway valve 2, which includes patient-end connection 3 including (by way of example only) combined respiratory flow sensor (pneumotachometer) and $CO_2$ sensor (capnometer) 80 and respiratory circuit-end connection 4, which connection allows the valve to be connected to, respectively, a patient (not shown) and anesthesia machine, ventilator circuit or other respiratory circuit (not shown). The tubing loop and airway valve combination may be sold as a pre-packaged assembly for one-time use. The particular design of valve 2 is not critical to the present invention, but preferred airway valve configurations are disclosed in the aforementioned U.S. patent application Ser. No. 09/173,517. In general, valve 2 is configured to allow gases to flow directly between patient connection 3 and ventilator circuit connection 4 during normal breathing or ventilation, but to selectively divert expired gases into tubing loop 1 to be stored for re-breathing, and to divert such stored, expired gases from tubing loop 1 to patient connection 3 for re-breathing. Tubing loop 1 is depicted as a loop of corrugated tubing. However, any type of tubing in which a volume change may be accomplished by lengthening or shortening the tube may be used. Tubing with corrugations or with helical pleats may be used. A tubing loop including one or more telescoping sections may also be employed. It is preferred, but not required, that the tubing itself retain the length to which it is set without external assistance. In the case that the tubing does not retain the length to which it is set, external means for holding the tubing at the desired length (e.g. ties, clamps, etc.) may be provided.

Card 10 is made from a sheet of substantially inelastic, lightweight and preferably disposable material, such as cardboard or plastic, the sheet having a size and shape such that it may lie adjacent to tubing loop 1 for adjustment to all desired length (volume) settings, from the minimum to the maximum. Any substantially planar, elongated structure which fulfills the functional requirements of the invention as described subsequently can be used in place of card 10, and is considered to fall within the scope of the invention. Although it is preferred that card 10 is formed of a substantially rigid material (i.e., a material which is rigid enough to be self supporting such as cardboard or plastic) a non-rigid material such as paper, fabric, or Tyvek®, can be used providing it is sufficiently durable to perform the functions described herein and, most significantly, substantially inelastic, since stretching of the material may lead to incorrect indication of tube length settings. Tubing loop 1 is shown at its minimum length in solid lines in FIG. 1, and at its maximum length in dashed lines. Several position templates indicating various lengths to which tubing loop 1 can be extended in order to obtain different, predetermined volumes are marked on card 10. In the example shown in FIG. 1, three generally U-shaped position templates over which the bight 1b of tubing loop 1 may be extended, respectively indicated by reference numbers 21, 22, and 23 are marked on card 10, but any practical number of position templates may be marked on card 10, as desired. Adjacent to position templates 21, 22, and 23, is text 31, 32, and 33, indicating the loop size, volume, or other desired information regarding the respective position template. Numbers, symbols or other indicia can be used to identify the different templates. Other information relating to use of the tubing loop valve assembly unit, manufacturer, etc., may be printed or otherwise marked on the card 10. In particular, it is preferred that instructions for use of the device are printed on the card. By having the instructions printed on a card which is attached to the device the chance of the user losing and/or failing to read the instructions (as could occur with instructions provided separately) is greatly reduced, and potential for incorrect usage of the device is minimized. The card may also include instructions for use of a monitoring device and/or other instructions.

In the embodiment shown in FIG. 1, first end 9 of card 10 is attached to airway valve 2. Alternatively, card 10 may be attached to a portion of tubing loop 1 or to any other part of the breathing or ventilator circuit, providing it is fixed in relationship to a portion of tubing loop 1 and does not impede lengthening and shortening of tubing loop 1.

Figure 2:
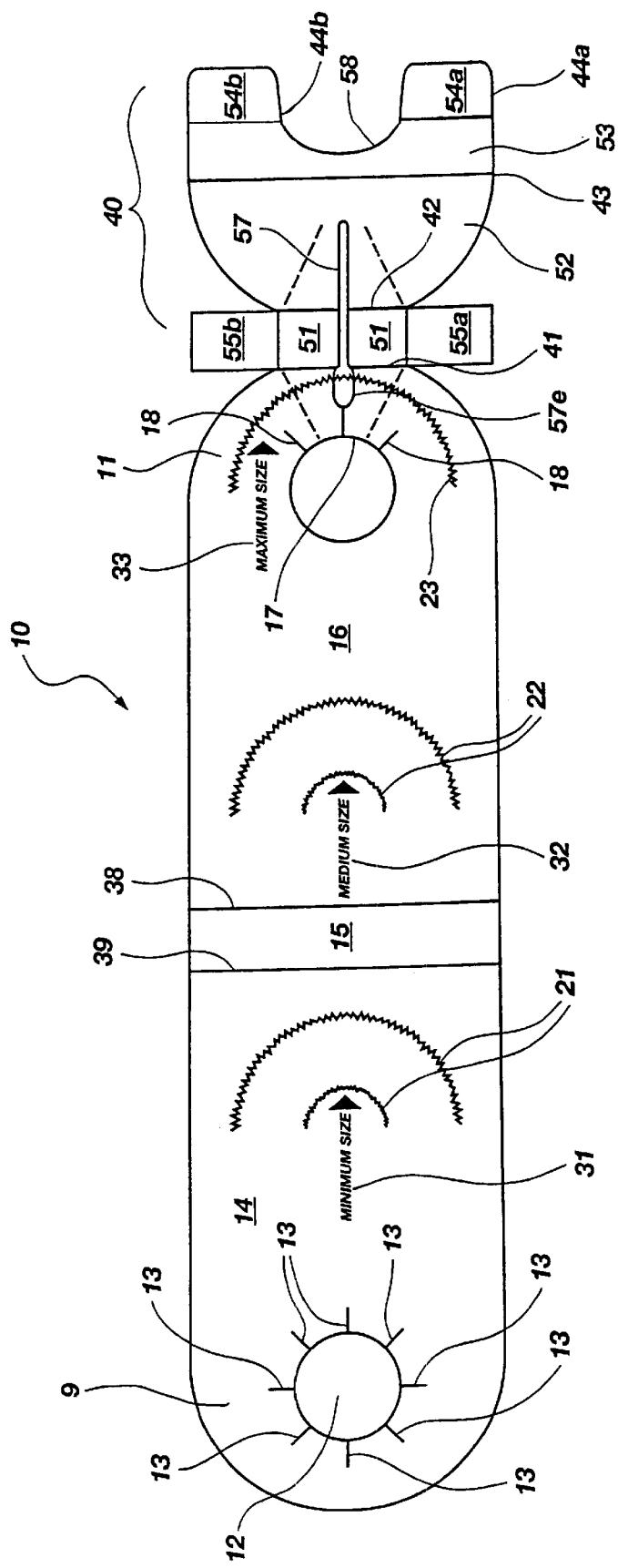
FIG. 2 shows the layout of the card of a first embodiment of the inventive device prior to assembly.
Figure 3:
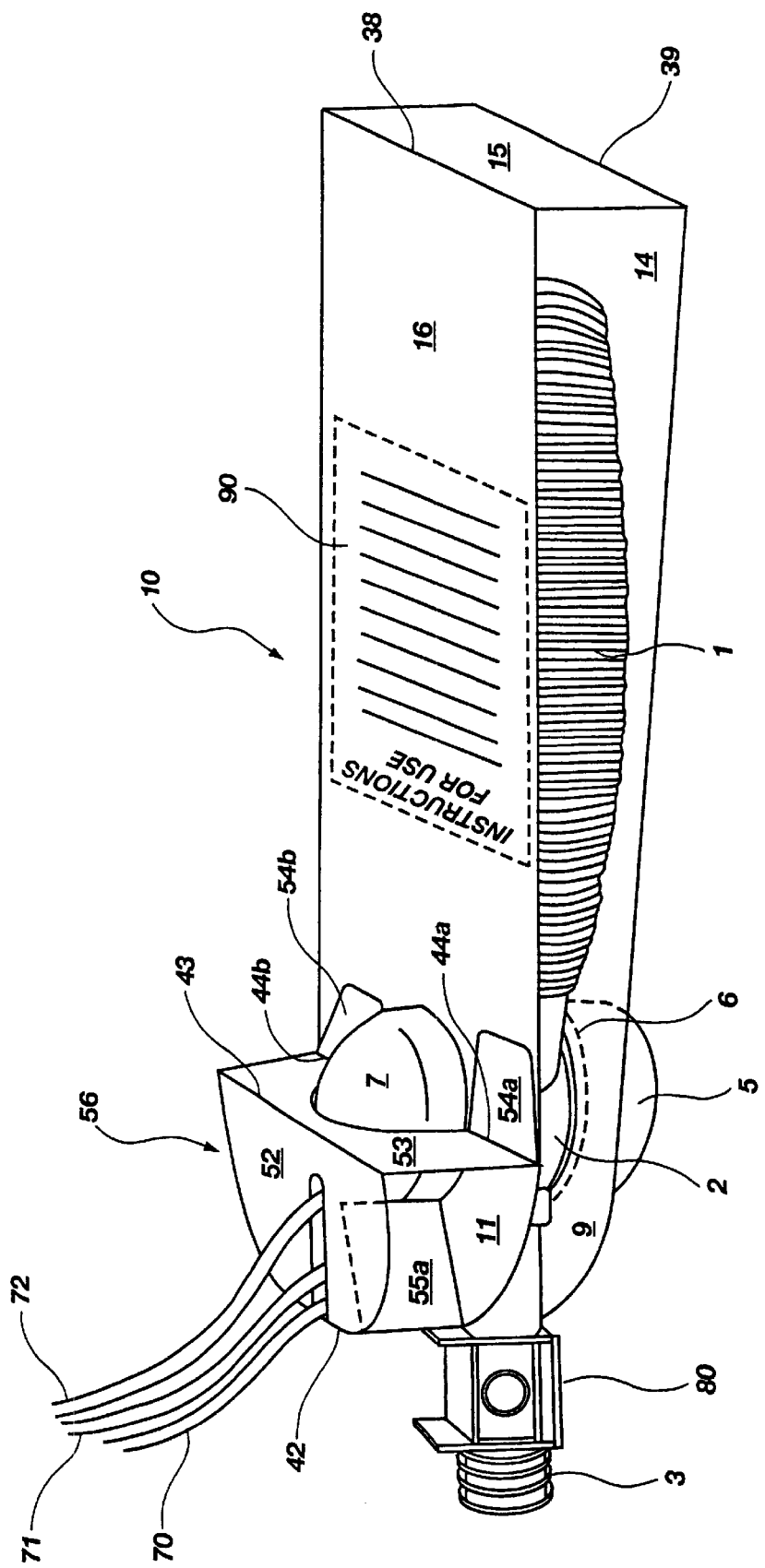
FIG. 3 shows the first embodiment of the inventive device folded around a tubing loop/valve assembly unit to provide protection during shipping and handling.

Card 10 is preferably attached to valve assembly 2 or tubing loop 1, or other part of a respiratory circuit, as described above, in such a way that all or most of card 10 can be readily removed after tubing loop 1 has been set to the desired length and volume. In the embodiment of the invention as illustrated, card 10 is attached to airway valve 2 by means of opening 12 in first end 9, illustrated in FIG. 2, which is press-fit over a protruding portion 5 of airway valve 2, as shown in FIG. 3. An example of the presently preferred design of card 10 is shown in FIG. 2. A side view of the card in use in a storage mode, folded around the tubing loop and airway valve assembly is shown in FIG. 3. Opening 12 includes radial slits 13 which allow the card material surrounding opening 12 to flex to better fit over protruding portion 5. Card 10 in the vicinity of opening 12 is pressed down onto protruding portion 5 until the edges of opening 12 are seated behind lip 6 of protruding portion 5. In the example shown, protruding portion 5 extends slightly further outward than the adjacent region to form lip 6. Alternatively, the edges of opening 12 could be seated in a channel or indentation in protruding portion 5 or behind a ridge or other protuberance on protruding portion 5. As shown herein, card 10 can be easily attached to or detached from protruding portion 5 using opening 12.

Alternatively, card 10 may be attached more permanently to the tubing loop and airway valve assembly (e.g., by assembling card 10 with opening 12 disposed between the body of airway valve 2 and protruding portion 5), in which case card 10 may optionally include a perforation near first end 9 to allow a larger portion of the card to be detached from the portion attached to the valve and/or tubing loop.

In one embodiment of the invention, card 10 is made sufficiently long and of a configuration so that it can be folded around tubing loop 1 to support and protect it during shipping and handling. It is preferred to construct card 10 in this manner when card 10 is used with a valve/tubing loop assembly which includes protruding parts which may be vulnerable to damage during shipping and handling. In FIG. 3, card 10 is folded along fold lines 39 and 40, to form first side 14, end panel 15, and second side 16 which enclose tubing loop 1. Second end 11 of card 10 includes an opening 17 which fits over protruding portion 7 of valve assembly 2. As shown in FIG. 2, opening 17 also includes radial slits 18 which allow the surrounding card material to flex and fit over protruding portion 7 of valve 2. In this embodiment, second end 11 includes extension 40, which is folded at fold lines 41, 42, 43, 44a and 44b to form panels 51, 52 and 53 and tabs 54a and 54b. Tabs 54a and 54b are glued to the exterior of side 16 to form a box-like structure 56. Support tabs 55a and 55b are folded inward to the positions indicated by the dashed lines on panels 16 and 52 and provide additional support for box-like structure 56. Referring again to FIG. 2, box-like structure 56 includes slot 57 which extends from opening 17 to fold line 41, through panel 51 to fold line 42, and part of the way through panel 52. Tubes 70 and 71, which lead in use to a pneumotachometer portion of combined sensor 80 are connected to nipples 81 and 82 thereof, which extend through enlarged portion 57e of slot 57 and extend upwardly through the narrower portion thereof for connection to a monitor (not shown). Tube 72, which is employed to pneumatically actuate airway valve 2, likewise extends through narrow portion of slot 57 and connects to a nipple on protruding portion 7 on airway valve 2. Thus, connections between combined sensor 80, airway valve 2 and the tubes 70–72 fit into and are physically protected during shipping, handling and storage by box-like structure 56. Panel 53 includes an opening 58 which is contiguous with opening 17 and accommodates protruding portion 7 of valve assembly 2. It will be appreciated that openings 17 and 58, slot 57, and enlarged portion 57e can be modified to accommodate various configurations of valves, sensors, patient connections, and respiratory circuit connections, and that various configurations of support tabs may be used without departing from the intended scope of the invention. It will be appreciated that substantially rigid material (e.g. cardboard) would be preferable for card 10 when it is designed to be formed into a box-like structure as described in this example.

Card 10 is preferably sized to wrap or fold around tubing loop 1 when tubing loop 1 compressed to its minimum length, to protect tubing loop 1 during shipping and handling of the unit, with enhanced protection for valve assembly 2, patient connection 3, and associated structures provided by box-like structure 56 as shown in the embodiment of FIGS. 2 and 3.

Figure 4:
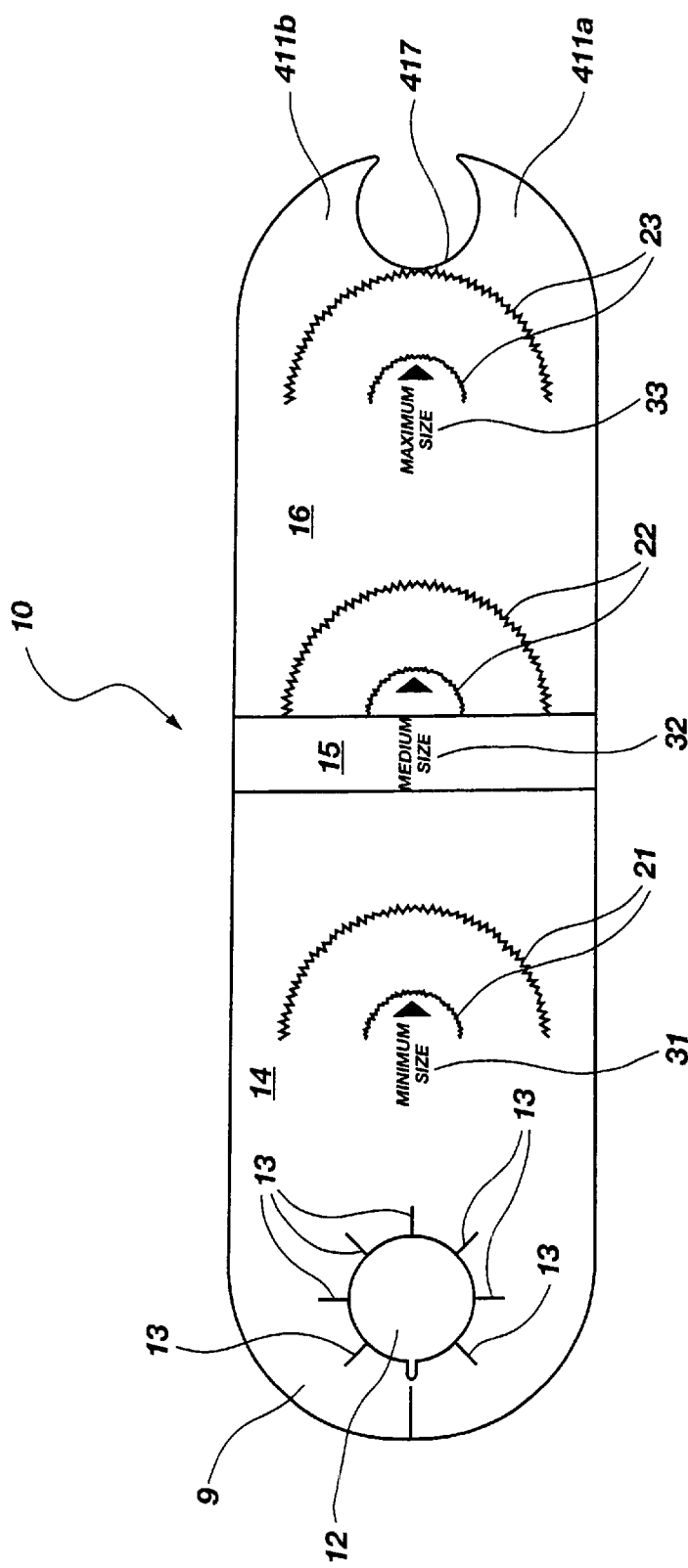
FIG. 4 shows the layout of the card for use in a second embodiment of the inventive device.
Figure 5:
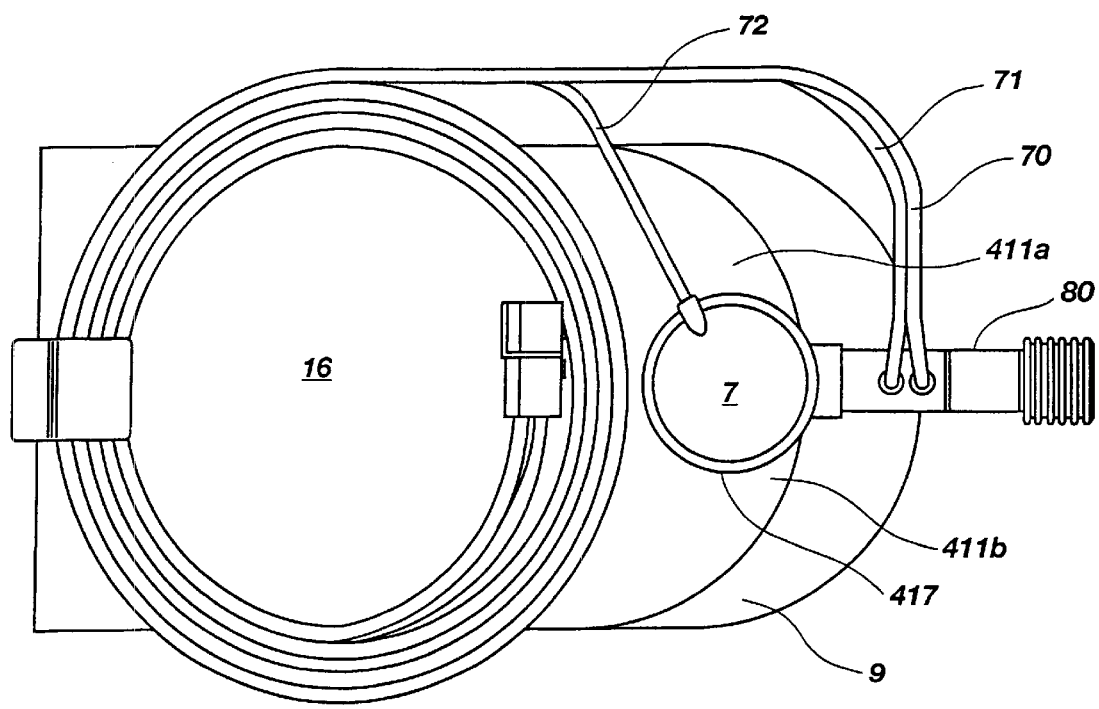
FIG. 5 shows a top view of the embodiment of FIG. 4, folded around a tubing loop/valve assembly unit.
Figure 6:
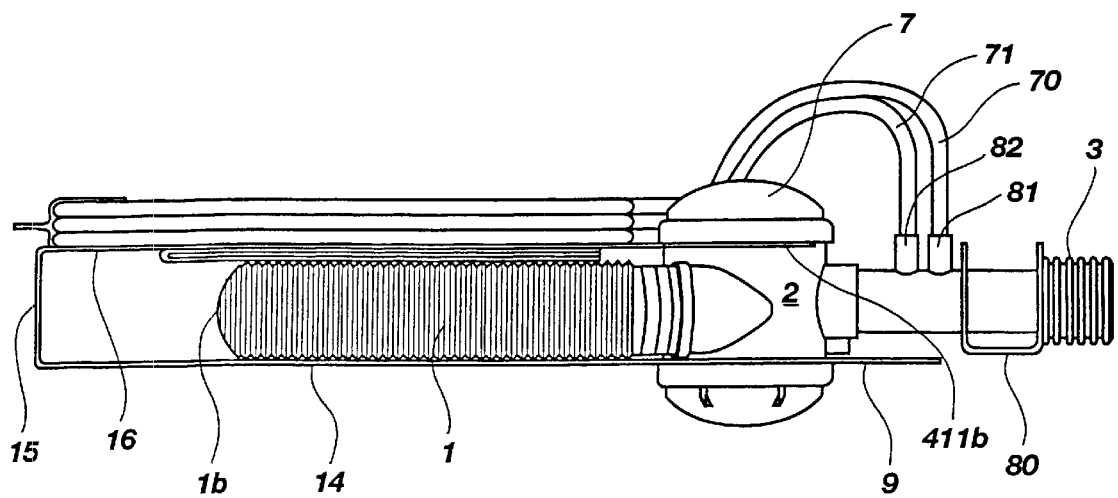
FIG. 6 is a side view of FIG. 5.

If a valve/tubing loop assembly is constructed in such a manner that further protection is not required during shipping and handling (e.g., the connection between valve 2 an tube 72 has a lower profile), a simpler template design shown in FIGS. 4–6 may be used. In the template design of FIGS. 4–6, the box-like structure 56 shown in FIG. 3 is omitted, and a semicircular opening 417 is provided which fits over projecting portion 7 of valve 2, as shown in FIGS. 5 and 6. Opening 417 is contiguous with the periphery of card 10, and projections 411a and 411b of panel 16 only partially enclose opening 417. Tabs 411a and 411b flex to allow opening 417 to fit around the projecting portion 7 of valve 2, and similarly permitting easy removal of card 10 from projecting portion 7. Other features (e.g., opening 12, position templates 21, 22 and 23 corresponding indicia 31, 32, 33, instructions for use of device printed on outer faces of card) of the embodiment of card 10 shown in FIGS. 4–6 are similar to the embodiment shown in FIGS. 1–3.

In the embodiment of the invention shown in FIGS. 4–6, position template 23 is located adjacent to opening 417 on the side closer to opening 12, rather than on the side opposite opening 17 as shown in FIGS. 1–3. This is because card 10 does not extend beyond opening 417 to provide an area on which to print position template 23. In the embodiment of FIGS. 4–6, the length of card 10 is increased between openings 12 and 417 to provide sufficient space to locate the position templates 21, 22 and 23 at the appropriate spacings. It will be appreciated that it would be possible to lengthen the card 10 in the embodiment of FIGS. 1–3 as well, if it were desired to print all position templates between openings 12 and 17, and that this would not effect the functioning of the template.

It is particularly advantageous to have instructions for use of the device printed on the outer faces of the card (as indicated at reference number 90 in FIG. 3) so that they are visible when it is folded around the tubing loop since the user must handle the card in order to remove it from the tubing loop, so the likelihood of the user reading the instructions is improved, and incorrect use with the potential for resulting patient injuries or death are consequently reduced. Instructions may also be printed on the inner face (i.e., the face with the templates marked on it) if desired. Prior to use of the tubing loop 1 and valve assembly 2, second end 11 of card 10 may typically be removed from valve assembly 2 and associated structures, and card 10 unfolded and flattened as shown in FIG. 1 to expose position templates 21, 22 and 23. Card 10 remains attached to the tubing loop 1 and valve assembly 2 at first end 9. Tubing loop 1 is then extended to match the appropriate template to achieve the desired volume setting, and card 10 then be removed from the tubing loop/valve assembly unit.

Alternatively, card 10 need not fold around tubing loop 1 to serve a packaging function, as in the preferred embodiments described herein, but may simply serve to provide a template for adjusting the length of tubing loop 1, in which case features at second end 11 which allow card 10 to also function as a package for the tubing loop/valve assembly unit would be omitted. In such an instance, card 10 may be made of a more robust material for re-use such as molded plastic, and ridges, pins or other protuberances may be molded therein. Alternatively, a more flexible, but non-elastic, material such as paper or fabric could be used if card 10 functioned as a template only, and not to provide support or packaging.

While the present invention has been described and illustrated in terms of certain specific embodiments, those of ordinary skill in the art will understand and appreciate that it is not so limited. Additions to, deletions from and modifications to these specific embodiments may be effected without departing from the scope of the invention as defined by the claims. Furthermore, features and elements from one specific embodiment may be likewise applied to another embodiment without departing from the scope of the invention as defined herein.

What is claimed is:

1. A device for calibrating a volume of a variable-length tubing loop for re-breathing use in a respiratory circuit, comprising:
 a card of substantially inelastic material comprising:
  a first face;
  a second face;
  a first end configured for affixation with respect thereto of a portion of a tubing loop extending over one of the first face and the second face of the card;
  a second end remote from the first end; and
  a plurality of template indicia marked on said first face of said card between the first end and the second end corresponding to a plurality of volumes to which said tubing loop may be adjusted by adjustment of tubing loop length.

2. The device of claim 1, wherein said first end comprises a perforation transversely thereacross at which said card may be torn to detach the remainder of said card from said first end.

3. The device of claim 1, wherein said card is constructed of cardboard.

4. The device of claim 1, wherein said card is constructed of plastic.

5. The device of claim 1, wherein said card is constructed of Tyvek®.

6. The device of claim 1, wherein said card is constructed of paper.

7. The device of claim 1, wherein said first end is configured for removable affixation with respect to said portion of said tubing loop.

8. The device of claim 1, wherein said card further comprises instructions for the use of said device and said variable-length tubing loop printed on at least one of said first face and said second face.

9. The device of claim 8, wherein said card further comprises instructions for the use of monitoring equipment used with said respiratory circuit.

10. The device of claim 7, wherein said first end comprises an opening having one or more slits into said card material extending from a periphery of said opening to permit said card material surrounding said opening to flexibly fit about a first portion of an airway valve associated with said tubing loop.

11. The device of claim 1, wherein said card is configured for folding around said tubing loop and an associated airway valve.

12. The device of claim 11, wherein said second end is configured for removable attachment to a first portion of said first airway valve to maintain said card in a folded configuration around said tubing loop and said airway valve.

13. The device of claim 11, wherein said second end comprises a box-like structure adapted to enclose a second portion of said airway valve.

14. The device of claim 13, wherein said box-like structure comprises an opening configured to fit over said second portion of said airway valve.

15. The device of claim 14, wherein said second end is folded and fastened upon itself to form said box-like structure; wherein said opening comprises one or more slits into said card material extending from a periphery of said opening to permit said card material surrounding said opening to flexibly fit over said second portion of said airway valve.

16. A device as in claim 15, wherein said box-like structure further comprises at least one slot configured to accommodate at least one element extending outwardly from said airway valve assembly.

17. A volume-adjustable tubing loop and valve assembly for use in facilitating re-breathing by a patient, comprising:
  a valve;
  a patient-end connection extending from said valve assembly;
  a respiratory circuit-end connection extending from said valve assembly;
  a tubing loop comprising a length of variable-length tubing attached at each of its ends to said valve;
  an elongated structure attached proximate a first end thereof to said valve and extendable therefrom adjacent and substantially parallel to said tubing loop, and having marked thereon a plurality of indicia indicating positions to which said tubing loop may be extended over said elongated structure to obtain specified internal tubing volumes associated with said indicia.

18. The tubing loop and valve assembly of claim 17, wherein said elongated structure is removably attached to said valve.

19. The tubing loop and valve assembly of claim 17, wherein said elongated structure is configured for selective folding to enclose said tubing loop.

20. The tubing loop and valve assembly of claim 19, wherein said elongated structure is configured for selective attachment proximate a second end thereof to said valve to maintain said elongated structure in a folded configuration.

21. The tubing loop and valve assembly as in claim 20, wherein said second end comprises a box-like structure configured for substantial enclosure of at least a portion of said valve.

22. A method of setting the length of a variable-length tubing loop for use in a ventilation circuit, comprising the steps of:
  fixing a portion of said tubing loop with respect to a structure bearing a plurality of templates, each said template of said plurality indicating a tubing loop length corresponding to an associated volume; and
  adjusting said tubing loop length to substantially match one of said templates.

23. The method of claim 22, comprising the further step of:
  removing said template-bearing structure from proximity with said tubing loop after said tubing loop has been adjusted to a length indicated by a template.

* * * * *

UNITED STATES PATENT AND TRADEMARK OFFICE
CERTIFICATE OF CORRECTION

PATENT NO. : 6,408,848 B1
DATED : June 25, 2002
INVENTOR(S) : Barry J. Feldman et al.

It is certified that error appears in the above-identified patent and that said Letters Patent is hereby corrected as shown below:

Title page,
Item [56], References Cited, OTHER PUBLICATIONS, change "Drawing" to
-- Drawings -- (in all references)

Column 1,
Line 9, change "non-invasive" to -- noninvasive --
Line 12, change "patients, and" to -- patients and, -- and insert a comma after "particularly"
Line 16, at the end of the line, delete "Non-"
Line 17, at the beginning of the line, change "invasive" to -- Noninvasive --
Line 19, change "non-invasive" to -- noninvasive --
Line 26, change "$CO_2$("p$CO_2$")," to -- $CO_2$ ("p$CO_2$"), --
Line 55, change "pre-setting" to -- Presetting --
Line 58, after "support" and before "for" insert -- during shipping and handling --
Line 61, delete the comma after "re-breathing" and delete "during shipping and handling"
Line 63, change "variable length" to -- variable-length -- and insert a comma after "loop"
Line 64, before "to" insert -- in order --
Line 66, after "for" and before "use" insert -- the --

Column 2,
Line 12, change "non-elastic" to -- nonelastic -- and before "a" delete "the"
Line 22, insert a comma after "instructions"
Line 57, after "loop" and before "and" insert -- 1 --
Line 58, after "valve" and before "combination" insert -- 2 --
Line 59, after "of" and before "valve" insert -- airway --
Line 63, at the beginning of the line, before "valve" insert -- airway --
Line 64, change "patient" to -- patient-end -- and change "circuit" to -- circuit-end --

Column 3,
Line 1, change "patient" to -- patient-end --
Line 11, insert a comma after "e.g."
Line 21, delete the comma after "10"
Line 25, change "non-rigid" to -- nonrigid --
Line 31, delete the comma after "1"
Line 50, insert a comma after "device"
Line 62, after "to" and before "valve" insert -- airway --

Column 4,
Line 32, change "39 and 40" to -- 38 and 39 --
Line 35, after "of" and before "valve" insert -- airway --
Line 38, after "of" and before "valve" insert -- airway --
Line 45, after "56" and before the period insert -- (see FIG. 3) --
Line 49, after "71" and before the comma insert -- (FIGS. 1 and 3) --

UNITED STATES PATENT AND TRADEMARK OFFICE
CERTIFICATE OF CORRECTION

PATENT NO.    : 6,408,848 B1
DATED         : June 25, 2002
INVENTOR(S)   : Barry J. Feldman et al.

It is certified that error appears in the above-identified patent and that said Letters Patent is hereby corrected as shown below:

Column 4 (cont'd),
Line 50, at the end of the line, after "82" insert -- (see FIG. 1) --
Line 51, after "57e" and before "of" insert -- (FIG. 2) --
Line 62, after "of" and before "valve" insert -- airway --

Column 5,
Line 2, insert a comma after "e.g."
Line 6, after "1" and before "compressed" insert -- is --
Line 8, after "for" and before "valve" insert -- airway --
Line 9, change "patient" to -- patient-end --
Line 14, after "between" and before "valve" insert -- airway -- and change "an" to -- and --
Line 19, change "projecting" to -- protruding --
Line 22, change "Tabs" to -- Projections --
Line 23, change "projecting" to -- protruding --
Line 25, change "projecting" to -- protruding --
Line 26, after "23" and before "corresponding" insert -- and --
Line 27, before "instructions" insert -- and -- and before "device" insert -- the --
Line 28, after "of" and before "card" insert -- the --
Line 42, change "effect" to -- affect --
Line 54, after "and" and before "valve" insert -- airway --
Line 56, at the beginning of the line, before "valve" insert -- airway --
Line 59, after "and" and before "valve" insert -- airway --
Line 61, after "10" and before "then" insert -- may --

Column 6,
Line 4, insert a comma after "re-use"
Line 6, at the end of the line, delete "non-"
Line 7, change "elastic" to -- nonelastic --
Line 8, delete the comma after "only"
Line 27, after "of" and before "tubing" change "a" to -- said variable-length --
Line 32, at the end of the line, after "said" insert -- variable-length --
Line 33, after "of" and before "tubing" insert -- a length of said variable-length --
Line 34, after "loop" delete "length"
Line 49, after "said" and before "tubing" insert -- variable-length --
Line 62, after "said" and before "tubing" insert -- variable-length --
Line 64, after "said " and before "tubing" insert -- variable-length --
Line 66, at the end of the line, after "is" insert -- further --

Column 7,
Line 1, at the beginning of the line, before "airway" delete "first" and before "folded" change "a" to -- said --
Line 2, after "said" and before "tubing" insert -- variable-length --

UNITED STATES PATENT AND TRADEMARK OFFICE
CERTIFICATE OF CORRECTION

PATENT NO. : 6,408,848 B1
DATED : June 25, 2002
INVENTOR(S) : Barry J. Feldman et al.

It is certified that error appears in the above-identified patent and that said Letters Patent is hereby corrected as shown below:

Column 7 (cont'd),
Line 3, change "11," to -- 12, --
Line 16, before "device" change "A" to -- The -- and change "as in" to -- of --
Line 19, after "valve" delete "assembly"
Line 22, after "valve" and before the semicolon insert -- assembly --
Line 28, after "valve" and before the semicolon insert -- assembly --
Line 30, after "valve" and before "and" insert -- assembly --

Column 8,
Line 2, after "said" and before "indicia" insert -- plurality of --
Line 5, after "valve" and before the period insert -- assembly --
Line 11, after "valve" insert -- assembly --
Line 12, before "folded" change "a" to -- said --
Line 13, change "as in" to -- of --
Line 16, after "valve" and before the period insert -- assembly --
Line 18, after "comprising" delete "the"
Line 19, delete "steps of"
Line 20, after "said" and before "tubing" insert -- variable-length --
Line 21, after "each" delete "said"
Line 22, after "plurality" insert -- of templates --
Line 25, after "said" and before "templates" insert -- plurality of --
Line 26, change "comprising the further step" to -- further comprising --
Line 27, delete "of"
Line 28, change "template-bearing structure" to -- structure bearing said plurality of templates --
Line 29, before "tubing" (both occurrences) insert -- variable-length --

Signed and Sealed this

Tenth Day of May, 2005

JON W. DUDAS
*Director of the United States Patent and Trademark Office*